(12) United States Patent
Toyoshima et al.

(10) Patent No.: US 7,347,847 B2
(45) Date of Patent: Mar. 25, 2008

(54) DISPOSABLE DIAPER CAPABLE OF BEING PUT ON EITHER FROM THE FRONT OR THE BACK OF A WEARER

(75) Inventors: Haruko Toyoshima, Tochigi (JP); Yasuyuki Okuda, Tochigi (JP)

(73) Assignee: Kao Corporation, Tokyo (JP)

( * ) Notice: Subject to any disclaimer, the term of this patent is extended or adjusted under 35 U.S.C. 154(b) by 193 days.

(21) Appl. No.: 10/626,559

(22) Filed: Jul. 25, 2003

(65) Prior Publication Data

US 2004/0243090 A1 Dec. 2, 2004

(30) Foreign Application Priority Data

Jul. 26, 2002 (JP) ............................. 2002-218959
Feb. 4, 2003 (JP) ............................. 2003-027631
May 16, 2003 (JP) ............................. 2003-139690

(51) Int. Cl.
*A61F 13/58* (2006.01)
(52) U.S. Cl. .................... 604/389; 604/385.03
(58) Field of Classification Search ................ 604/389, 604/385.01, 385.22–385.31
See application file for complete search history.

(56) References Cited

U.S. PATENT DOCUMENTS

| | | | | |
|---|---|---|---|---|
| 3,312,981 A | * | 4/1967 | McGuire et al. ............... | 2/406 |
| 3,616,798 A | * | 11/1971 | Garfinkel ..................... | 604/398 |
| 4,081,301 A | * | 3/1978 | Buell ......................... | 156/164 |
| 4,515,595 A | * | 5/1985 | Kievit et al. ............... | 604/385.3 |
| 4,578,071 A | * | 3/1986 | Buell ......................... | 604/379 |
| 4,681,580 A | * | 7/1987 | Reising et al. ............ | 604/385.3 |
| 4,904,249 A | * | 2/1990 | Miller et al. ................ | 604/378 |
| 5,034,008 A | * | 7/1991 | Breitkopf ................ | 604/385.27 |
| 5,234,423 A | * | 8/1993 | Alemany et al. ........ | 604/385.3 |
| 6,264,639 B1 | * | 7/2001 | Sauer .................. | 604/385.101 |
| 2002/0151863 A1 | * | 10/2002 | Toyoshima ............ | 604/385.29 |

FOREIGN PATENT DOCUMENTS

| | | |
|---|---|---|
| EP | 1184012 A1 | 3/2002 |
| EP | 1226802 A2 | 7/2002 |
| JP | 2-164363 A | 6/1990 |
| JP | 6-63077 A | 3/1994 |
| JP | 8-71103 A | 3/1996 |
| JP | 11-155906 A | 6/1999 |
| JP | 2000-254167 A | 9/2000 |
| WO | WO95/12376 A1 | 5/1995 |
| WO | WO00/53140 A1 | 9/2000 |

* cited by examiner

*Primary Examiner*—Tatyana Zalukaeva
*Assistant Examiner*—Laura C Hill
(74) *Attorney, Agent, or Firm*—Birch, Stewart, Kolasch & Birch, LLP

(57) ABSTRACT

A disposable diaper capable of being put on from either the front or the back of a wearer is disclosed. The longitudinal end section having the fastening tapes has a waist elastic member and an extensible side part. The absorbent member is disposed such that its longitudinal end in the section having the fastening tapes is nearer to the waist portion of that section than the centerline parallel to the diaper width direction and dividing each of the extensible side parts into equal halves. Two portions on opposite sides of the centerline dividing the length of the diaper in equal halves have a saturated absorption capacity ratio of 45/55 to 55/45. The natural length of the waist elastic member in the state removed from the diaper is 60 to 80% of the length of the waist elastic member as provided in the diaper.

4 Claims, 3 Drawing Sheets

DISPOSABLE DIAPER CAPABLE OF BEING PUT ON EITHER FROM THE FRONT OR THE BACK OF A WEARER

BACKGROUND OF THE INVENTION

The present invention relates to a disposable diaper that can be put on a wearer with ease whether the portion having fastening tapes (hereinafter referred to as a first section) goes in either the front or the back of the wearer and which hardly leaks when put on in either way.

Known disposable diapers include fitted diapers having fastening tapes and pull-on diapers (also called pants type diapers or all-in-ones) that can be put on like ordinary underwear. Fitted disposable diapers are most commonly used in view of their applicability to a full range of children, from newborns to toddlers, and because of their lower production cost. Fitted disposable diapers are generally designed such that the portion with fastening tapes (back portion) is placed in the back and the fastening tapes are fastened from the back onto a landing zone on the front portion to hold the diaper on securely.

This way of diapering, i.e., a back-to-front way of fastening, is easy on such a wearer as a baby or an infant lying still on its back. However, it is not easy on an infant who is active enough to, for example, crawl or roll, being reluctant to wear a diaper.

Pull-on disposable diapers are on the market for infants who can walk, but disposable diapers suited for babies who have mastered crawling and are now on to pulling themselves up are not available yet. Even after a baby becomes able to pull itself up on something into a standing position, it is practically difficult to make the baby raise one foot to put on a pull-on diaper.

Hence, the present inventors have attempted to use a conventional fitted disposable diaper backward, that is, put on the diaper with back portion going in the front. However, when a conventional fitted disposable diaper, which is designed for back-to-front fastening, is put on backward, it is less capable of exhibiting its absorbing ability and more liable to leak while worn than when put on in a normal back-to-front way. Moreover, a conventional fitted diaper designed for back-to-front diapering is difficult to put on backward.

JP-A-6-63077 proposes a disposable diaper which is designed to be fastened with fastening tapes on the wearer's back side. The diaper has an elastic flap on each side of the stomach portion and a fastening tape fixed to each of the elastic flaps and enjoys ease of fastening on the wearer's back side as compared with traditional fitted disposable diapers. Nevertheless one often finds it convenient to fix fastening tapes on the wearer's front side. Therefore a diaper configured exclusively for fastening on the back side cannot avoid sacrificing for ease of putting on the front side, both absorbing front side). The diaper of JP-A-6-63077 is designed for fastening only on the wearer's back side for application to infants who have developed to move actively and therefore gives no considerations to back-to-front fastening usage. Thus, a disposable diaper that sufficiently satisfies ease of putting on and absorption requirement when fastened on either way has not yet been proposed.

Fitted disposable diapers having a pair of extensible side parts are recently known as being easy to fasten on the stomach side, the extensible side parts each having a plurality of elastic members and being arranged on the inner side of each fastening tape. This type of disposable diapers give a snug fit as long as they are fastened on the stomach side. However, when they are put on backward, it turned out that bunching or wrinkling occurs between, or in the vicinity of, the extensible side parts, which generates a gap between the wearer's body and the diaper and easily causes leakage.

JP-A-2-164363 proposes a diaper cover which is designed to be fastened with fastening tapes on the wearer's back side. The diaper cover is not provided with an absorbent member in a unitary manner, and is to be used by placing a diaper at an appropriate portion of the cover. Due to this constitution, the diaper tends to slide down from the placed position and leakage tends to occur. The fastening tape is difficult to pull, and the diapering operation is not easy in the case of back side fastening usage. Even if one fastens the fastening tape on the infant's back side with some effort, the diaper cover fails to follow the infant's movement and tends to slide down due to unconformity to the change in the waist size of the infant. Furthermore, the diaper is designed to be fastened on the wearer's back side, and no consideration is given to front side fastening usage.

WO95/12376 discloses a diaper having a pair of fastening ears which extend to the wearer's back side. Due to the constitution that the diaper is fastened on the wearer's back side, there is a fear of leakage when it is fastened on the front side. The ears largely shrink when the wearer puts on the diaper, which does not provide good diapering.

SUMMARY OF THE INVENTION

The present invention relates to a disposable diaper capable of being put on from either the front or the back of a wearer which includes a liquid permeable topsheet, a liquid impermeable backsheet, a liquid retentive absorbent member interposed between the topsheet and the backsheet, the diaper having a pair of longitudinal side portions and a pair of longitudinal end sections with each respective side portion and said each longitudinal end section having a side edge, and a crotch section located between the longitudinal end sections, and a fastening tape provided on each side edge of one of the longitudinal end sections thereof, wherein, the longitudinal end section having the fastening tapes has a waist elastic member provided in a waist portion thereof to form an extensible waist part, the longitudinal end section having the fastening tapes has an extensible side part formed in each of a pair of side areas at a below-waist portion thereof, the absorbent member is disposed such that its longitudinal end in the longitudinal end section having the fastening tapes is nearer to the waist portion of that section than a centerline parallel to a diaper width direction and dividing each of the extensible side parts into equal halves, a width of the absorbent member located between the pair of extensible side parts is equal to or greater than a minimum width of the absorbent member located in the crotch section of the diaper, two portions on opposite sides of a centerline dividing the length of the diaper in equal halves have a saturated absorption capacity ratio of from 45/55 to 55/45, and a natural length of the waist elastic member in a state removed from the diaper is from 60 to 80% of a length of the waist elastic member as provided as part of the diaper.

BRIEF DESCRIPTION OF THE INVENTION

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

The present invention will be described in detail with reference to its preferred embodiment. All publications cited herein are hereby incorporated by reference.

The present invention relates to a disposable diaper that can easily be put on a wearer from either the front or the back of the wearer, that is, with its portion having fastening tapes going in either the back or the front of a wearer and which hardly leaks in either way of diapering.

Figure 1:
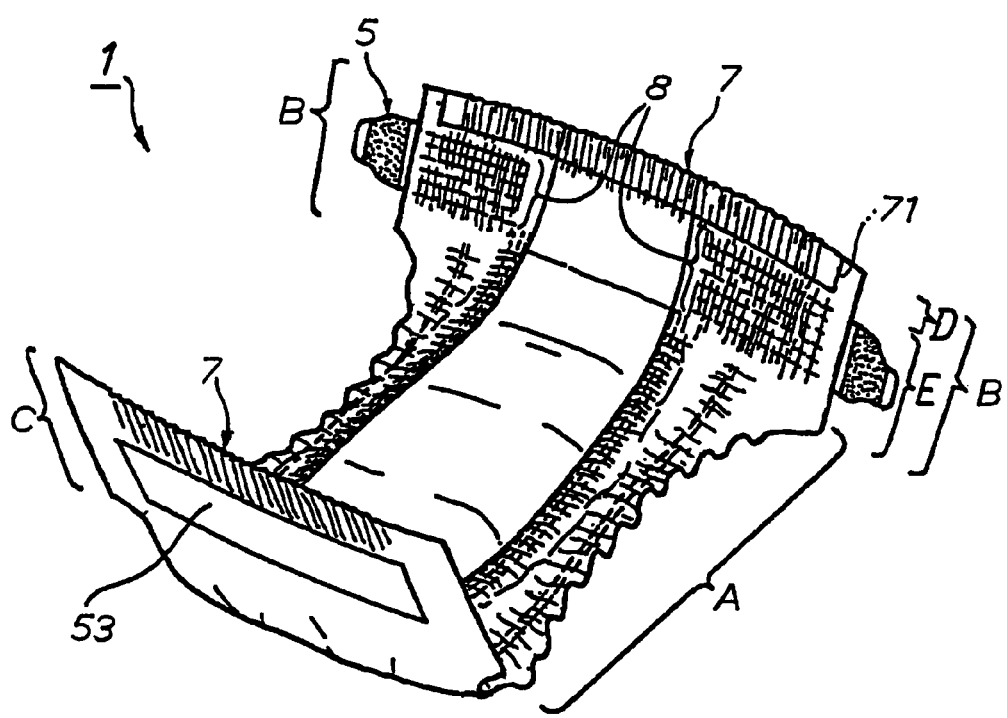
FIG. 1 is a perspective view of a disposable diaper according to an embodiment of the present invention.
Figure 2:
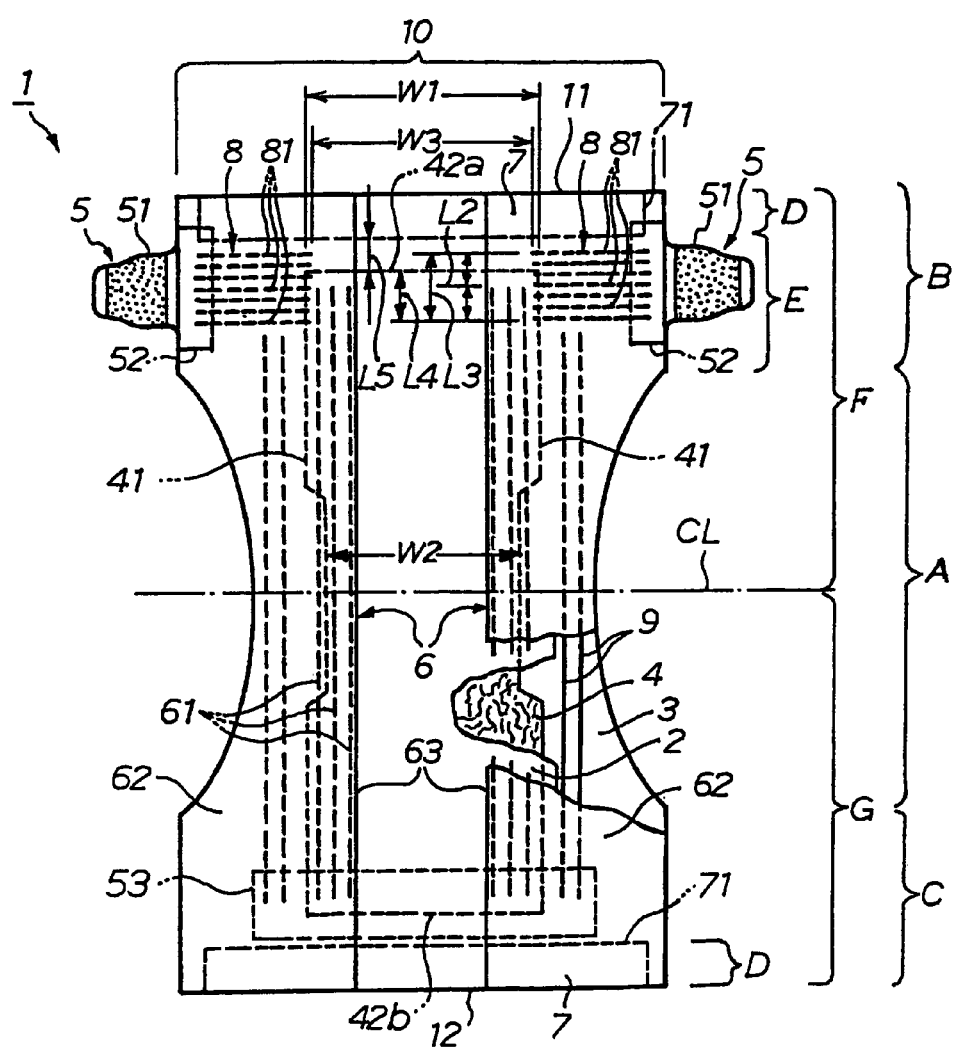
FIG. 2 is a plan view of the disposable diaper of FIG. 1 with a part cut away, in which every elastic member is stretched substantially flat.

A preferred embodiment of the present invention provides a disposable diaper 1 shown in FIGS. 1 and 2 which includes a liquid permeable topsheet 2, a liquid impermeable backsheet 3, and a liquid retentive absorbent member 4 interposed between these two sheets. The disposable diaper 1 is of a fitted type. It is divided in the width direction into a crotch section A in the middle in the length direction, a first section B on one side of the crotch section A, and a second section C on the other side of the crotch section A. The first section B has a pair of fastening tapes 5 each provided on each side edge thereof, and the second section C has a landing zone 53 for receiving the fastening tapes 5. The crotch section A is applied to the crotch of a wearer. Either one of the first section B or the second section C goes in the back of a wearer, and the other in the front (the stomach side).

The crotch section A describes an inward arc on both sides thereof The disposable diaper 1 as a whole has a sand or hour glass-shape with its longitudinal middle portion narrowed.

The topsheet 2 is substantially rectangular and larger than the absorbent member 4 when viewed from above. The absorbent member 4 is arranged in the middle of the width of the backsheet 3. The backsheet 3 is sand glass-shaped in agreement with the contour of the diaper 1.

The topsheet 2 and the backsheet 3 both extend outward from the two longer sides 41 and two shorter sides 42a and 42b of the absorbent member 4 and are bonded together in these extensions. The backsheet 3 extends outward from the two longer sides of the topsheet 2.

A pair of standing gathers (also called cuffs) 6 are provided on both longitudinal side portions of the diaper 1. The pair of standing gathers 6 are each formed of a gather-forming sheet 62 having elastic members 61, the gather-forming sheet 62 being disposed to cover both side areas of the longer side edge of the topsheet 2. Each sheet 62 is fixed to the topsheet 2 in a straight line pattern parallel to the diaper in its longitudinal direction. The straight line is positioned between (a) a straight line connecting the side edge 41 of the absorbent member 4 in the first section B and that in the second section C and (b) the laterally most inward elastic member 9 (described later) arranged in the leg portion. The linear joint of the sheet 62 with the topsheet 2 is a fixed end of the standing gathers 6. The part of the sheet 62 extending outward from the fixed end is fixed to the topsheet 2 or the backsheet 3. In the areas near the two longitudinal ends of the diaper 1, the part of the sheet 62 extending inward from the fixed end is fixed to the topsheet 2. The elastic members 61 used to form the standing gathers 6 are elastic threads. A plurality of the elastic members (threads) 61 are arranged per side substantially in parallel with the free end 63 of the standing gathers.

The first section B has a waist portion D and a below-waist portion E. An elastic member 71 is provided in the waist portion D to form an extensible waist part 7. A plurality of elastic members 81 are provided on each side area of the below-waist portion E to form a pair of extensible side parts 8. All the elastic members 71 and 81 are arranged in parallel with the diaper width direction.

The waist portion D constitutes the longitudinal end portion of the diaper 1 and is applied to the waist of a wearer. More specifically, an area from the longitudinal end to 20 mm inward is called a waist portion D. The diaper 1 according to this embodiment has the extensible waist part 7 formed by the waist elastic member 71 in the waist portion D in both the first and second sections B and C. The waist elastic member 71 in each waist portion D is fixed between the backsheet 3 and the topsheet 2 or the sheet 62 in its stretched state across the diaper. The waist elastic member 71 used in this embodiment is about 10 to 30 mm wide and about 1 to 3 mm in thickness, made of a strip of urethane foam. Within this thickness range of the waist elastic member 71, the first section B is better prevented from forming a gap with the wearer's body or bunching up.

In FIG. 2 that is a plan view of the disposable diaper 1 with all its elastic members in their stretched state, the upper part of the diaper 1 is designated first section B, and the lower part second section C. The below-waist portion E of the first section B is located below the waist portion D (20 mm wide from the top end downward) and above the crotch section A which is applied to the crotch of a wearer and describes an inward arc on both sides thereof in conformity with the wearer's thighs. The "side area of the below-waist portion E" as referred to above means the area located within the below-waist portion E and along the longer side of the diaper. The plurality of below-waist elastic members 81 are arranged per extensible side part 8 in parallel to the diaper width direction at prescribed intervals.

The elastic members 81 are fixed in their stretched state such that elastic extensibility may develop in at least areas extending outward from both side edges 41 of the absorbent member 4 in the diaper width direction. The below-waist elastic members 81 are not disposed in the middle portion of the area between the longer side edges 41 of the absorbent member 4. The elastic members 81 are fixedly sandwiched in between two soft sheets (not shown) which are provided in the first section B over the width of the main body 10. The term "main body (10) of the diaper (1)" as used herein means the part composed of the topsheet 2, the backsheet 3, and the absorbent member 4 and including all the sections A to C. The two sheets are fixed by bonding between the backsheet 3 and the topsheet 2 or the gather-forming sheet 62. The inward end of each below-waist elastic member 81 is positioned slightly inward from the side edge 41 of the absorbent member 4. Therefore, there is no elastic member 81 laid in the area from the middle in the width direction of the absorbent member 4 up to a position near each side edge 41.

The fastening tape 5 has a sticking part 51 which sticks out from the side edge of the first portion B and a basal part 52 which is wider than the sticking part 51 and fixed between two sheets of the main body 10. The below-waist elastic members 81 and optionally the waist elastic member 71 are disposed in the area between the two basal parts 52. By this configuration, the force imposed to the fastening tapes 5 is transmitted to at least the below-waist elastic members 81 and is effective. A plurality of leg elastic members 9 are arranged linearly in the diaper length direction on each longer side portion of the diaper 1 to form leg gathers.

Crosswise sectioned into two equal halves F and G along the centerline CL (see FIG. 2), the disposable diaper 1 is designed to have substantially equal absorbency between the sections F and G. More concretely, the ratio of saturated absorption capacity of the halves, F/G, ranges from 45/55 to 55/45, preferably from 48/52 to 52/48. As a result, urine leakage does not occur irrespective of whether the diaper is put on in a back-to-front way (the first section B goes in the back of a wearer, and the fastening tapes 5 are fixed onto the landing zone 53 on the stomach) or in a front-to-back way (the first section B goes in the front of a wearer, and the fastening tapes 5 are fixed onto the landing zone 53 on the back of the wearer). If the F/G saturated absorption ratio is out of the above range, the diaper is leaky depending on or regardless of which way of diapering is followed. In order to prevent leakage irrespective of the way of diapering, it is preferred that the difference in saturated absorption capacity between the F and G sections be as small as possible.

In the present embodiment, the distance from the longitudinal end 11 of the diaper 1 to the longitudinal end 42a of the absorbent member 4 in the first section B and the distance from the other longitudinal end 12 of the diaper 1 to the other longitudinal end 42b of the absorbent member 4 in the second section C are substantially equal. The difference between these distances if any is preferably 20 mm or smaller, still preferably 10 mm or smaller.

The saturated absorption capacity of the section on each side of the centerline CL is measured as follows.

Method of measuring saturated absorption capacity:

A diaper 1 is cut across into two along the centerline CL, the line dividing the length of the diaper into equal halves. The standing gathers, the leg gathers, and the extensible side parts in the below-waist portion are cut off from each half. Care should be taken to keep the structure of the absorbent member intact. The cut piece is placed on a metal net which is configured to be taken out of a container horizontally. The metal net with the cut piece on is weighed and then put in a container having a drain hole in the lower part of one side thereof The drain hole is closed, and 0.9 wt % of physiological saline is poured to completely immerse the absorbent member at a rate controlled so that polymer particles and the like may not fall off from the cut edge of the diaper. After being completely immersed, the cut piece is allowed to stand for 30 minutes. The container is tilted 100 with the drain hole side down, and the drain hole is opened to discharge the liquid. The container is kept tilted for 30 minutes until the liquid is completely drained. The metal net with the cut piece on is taken out of the container and weighed again. The difference between the weight after immersion and the weight before immersion is taken as a saturated absorption capacity (g) of the cut piece.

As shown in FIG. 2, the absorbent member 4 is disposed such that its longitudinal end 42a in the first section B is nearer to the waist portion D of that section than the centerline L2 across the extensible side parts 8. The centerline L2 across the extensible side parts 8 is a line parallel to the diaper width direction and dividing the distance L3 between the below-waist elastic member 81 nearest to the waist elastic member 71 and the below-waist elastic member 81 farthest from the waist elastic member 71 in each extensible side part 8 into equal halves.

In order to further secure safetyagainst leakage due to the generation of a gap between the wearer's body and the inner surface of the diaper, especially when the diaper is put on with the first section B on the stomach side, the ratio of the distance L4 (see FIG. 2) to the distance L3 is preferably from 50 to 100%, still preferably from 65 to 100%, wherein the distance L3 is as defined above, and the distance L4 is the distance between the longitudinal end 42a of the absorbent member 4 in the first section B and the straight line connecting a pair of below-waist elastic members 81 which are the farthest from the diaper end 11 in the first section B. It is also preferred for the same purpose that the distance L5 (see FIG. 2) be 30 mm or smaller, particularly 0 to 20 mm, wherein the distance 5 is the distance between the longitudinal end 42a of the absorbent member 4 and the nearer longer side edge of the waist elastic member 71 in the first section B.

It should be noted that the "longitudinal end 42a of the absorbent member 4 in the first section B" is to mean the longitudinal end of the part of the absorbent member 4, the part existing in the area between the pair of extensible side parts 8 and having substantially the same stiffness as the part of the absorbent member 4 existing in the crotch section A. In particular, the absorbent member 4 existing between the pair of extensible side parts 8 preferably has a bending stiffness (JIS K7171) within a specific range as stated below.

The width W1 (see FIG. 2) of the absorbent member 4 in the area between the pair of extensible side parts 8 is equal to or greater than the minimum width W2 (see FIG. 2) of the absorbent member 4 in the crotch section A. Where the below-waist elastic members 8 overlap the side of the absorbent member 4 as in the embodiment shown in FIG. 2, the width W1 is the total width inclusive of the overlap(s), provided that the width W1 is measured on the part of the absorbent member with substantially the same stiffness as the part of the absorbent member in the crotch section A. A preferred stiffness of the absorbent member and a method of measuring the stiffness will be described later. It is preferred for the absorbent member 4 to have its middle portion in the length direction narrowed as in the present embodiment. In other words, the width W1 is preferably greater than the minimum width W2.

The length of the waist elastic member 71 in the state removed from the diaper 1 (hereinafter referred to as a natural length) is preferably from 60 to 80%, more preferably from 65 to 75%, of its length as disposed in the diaper 1 and measured in the state stretched substantially flat as illustrated in FIG. 2 (hereinafter referred to as a stretched length). If the natural length is less than 60% of the stretched length, the elastic member 71 as fixed gathers in excess around the waist portion that the diaper is difficult to bring into conformity with the wearer's body. If, on the other hand, the natural length is more than 80% of the stretched length, the extensibility is insufficient for easily fastening the fastening tapes onto the second section C.

In the present embodiment, the tensile load required to extend the below-waist portion E in the first section B to an extension ratio 30% lower than the maximum extension ratio (hereinafter referred to as a tensile load of the below-waist portion E) is higher than that required to extend the waist portion D in the same section to an extension ratio 30% lower than the maximum extension ratio (hereinafter referred to as a tensile load of the waist portion D). When so designed, the disposable diaper of the present invention exhibits especially pronounced effects as intended in the invention. The tensile load of the below-waist portion E is preferably from 80 to 500 gf, still preferably from 150 to 400 gf, and the tensile load of the waist portion D is preferably from 50 to 400 gf, still preferably from 100 to 300 gf.

The above-identified tensile loads of the below-waist portion E and the waist portion D are measured as follows.

Method of measuring tensile load of below-waist portion E:

The below-waist portion E containing all the below-waist elastic members 81 is cut out across the main body 10 (see FIG. 2). In this particular embodiment, the below-waist portion E is the portion below the 20 mm-wide area from the longitudinal end 11 (in the first section B) inward and between both main body 10's side edges from which the fastening tapes stick out. The cut piece (specimen) is extended in the diaper width direction on a Tensilon tensile tester RTA-100, supplied from Orientec. The specimen is clamped in the jaws set at an initial distance 50 mm shorter than the natural width (referred to as the initial length) of the first section as measured with no force applied thereto. The specimen is pulled at a crosshead travel speed of 300 mm/min up to its maximum extension length. The term "maximum extension length" as used herein means the length of the specimen from which all the elastic members have been removed, that is, the length of the specimen with no gathers. The maximum extension ratio P (%) of the sample is obtained from [(maximum extension length–initial length)/initial length] ×100. The tensile load (tensile force) at an extension ratio 30% lower than the maximum extension ratio P is read.

Method of measuring tensile load of waist portion D:

The waist portion D is cut out from the first section B across the main body 10 (see FIG. 2). In this particular embodiment, the waist portion D is an area from the longitudinal end 11 to 20 mm inward and between both main body 10's side edges from which the fastening tapes stick out. The tensile load (tensile force) of the waist portion D at an extension ratio 30% lower than the maximum extension ratio P is obtained in the same manner as for the below-waist portion E. In case the difference obtained by subtracting 30% from the maximum extension ratio P, namely, (P-30)% is negative, the tensile load (tensile force) is regarded to be 0 gf.

The width W3 (see FIG. 2) of the area where the below-waist elastic members 81 are not provided, that is, the area showing no elastic extensibility in the first section B is preferably half to equal the absorbent member width W1 and is preferably one-fifth to one-third the whole width of the first section B. This is preferred for improving ease of diapering in the back-to-front manner and/or the front-to-back manner and for securing safety against leakage.

In the present embodiment, it is preferred for the absorbent member to have stiffness within a specific range at least in its part located between the extensible side parts 8. More specifically, a specimen of the absorbent member 4 cut out of the area from its longitudinal end 42a (in the first section B) to 50 mm inward preferably has a flexural stiffness of from 3 to 25 gf/50 mm, particularly from 5 to 25 gf/50 mm, in the diaper width direction. Such stiffness is preferred for ensuring the ease of diapering, having a snug fit, and reduced leakage regardless of the diapering direction and also for providing a wearer with comfort. Where in particular the tensile load of the below-waist portion falls within the above-recited range, there is no impaired extensibility of the extensible side parts, and the diaper will offer a snug fit while giving a gentle touch to the below-waist portion of a wearer's body.

The flexural stiffness in the diaper width direction is measured as follows.

Measurement of flexural stiffness:

A 50 mm wide and 80 mm long specimen of the absorbent member has all the other constituent members including from the topsheet to the backsheet except the standing gathers is cut out of the diaper from the area from the longitudinal end 42a of the absorbent member 4 (in the first section B) to 50 mm inward. The 80 mm length of the specimen is in the diaper width direction. Care should be taken so that the specimen has no crease or wrinkle that may influence the measurement. Where the width W1 of the absorbent member is smaller than 80 mm, the whole width W1 will be the length of the specimen.

Measurement is carried out with a Tensilon tester, RTC-1150A supplied by Orientec, equipped with a 5-kg load cell (range: 200 gf) in accordance with JIS K7171 (Plastics—Determination of flexural properties) (R1=5.0±0.1 mm, R2=±0.2 mm). The specimen is placed on two supports 50 mm apart with its length being along the line connecting the two supports, and an indenter is positioned to just touch the mid-point of the specimen. The indenter is moved down at a speed of 30 mm/min to obtain a load-deformation curve. The maximum of the flexural stress is taken as a bending flexural stiffness (gf/50 mm).

The disposable diaper according to the present invention has a pair of extensible side parts provided in each side part of the below-waist portion of the first section B (one of the two end sections of the diaper crosswise sectioned into three) and exhibits substantially equal absorbency between halves on both sides of the crosswise centerline CL of the diaper. According to this design, the diaper can easily be put on a wearer whether the first section B goes in the back or the front, and the diaper hardly leaks from the front of a wearer, where the wearer's urethra is, regardless of the direction of diapering.

Figure 3:
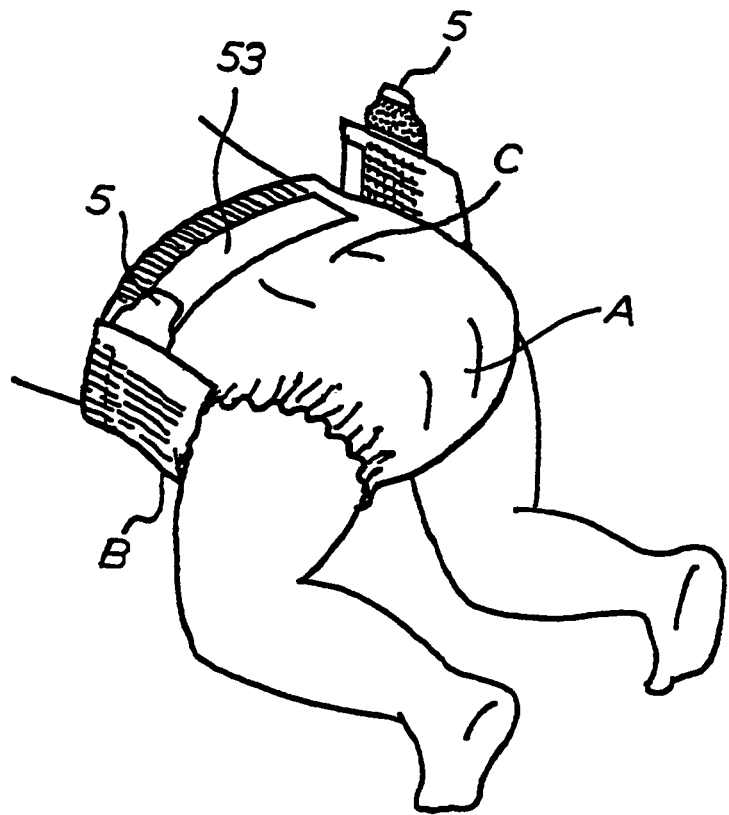
FIG. 3 is a perspective view illustrating the disposable diaper of FIG. 1 being put on from the back of an infant.
Figure 4:
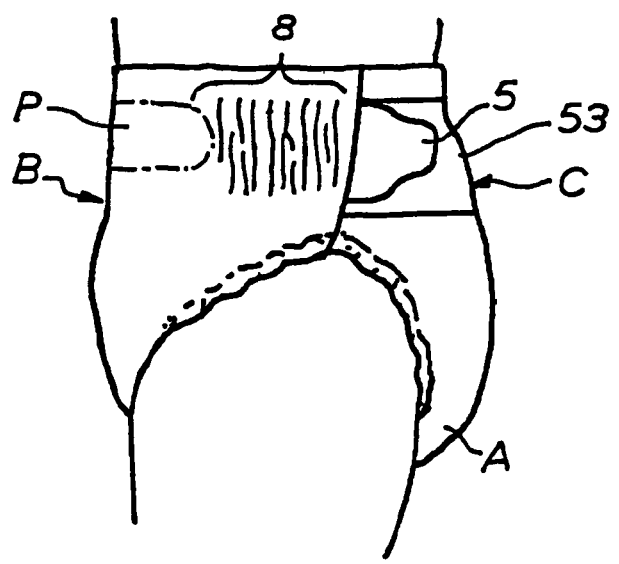
FIG. 4 is a side view of the disposable diaper of FIG. 1 put on a standing infant with the first section B going in the front.

The disposable diaper of the present invention is easy to put on a wearer no matter what position the wearer is in, either lying on its back or stomach, or standing facing or not facing the person trying to place the diaper. The diaper is easy to put on even when a baby or an infant rolls or crawls (see FIG. 3) when trying to escape from being diapered. FIG. 4 illustrates the diaper 1 put on an infant in a standing position with the first section B on the stomach (in a front-to-back way). The language "easy to put on either from the front or the back of a wearer" means that a disposable diaper is easy to put on a wearer irrespective of whether the section with the fastening tapes 5 (namely, the first section B) goes in the back or the front of the wearer.

In addition, the absorbent member 4 with a certain stiffness and a relatively large width occupies a major part of the area between the pair of extensible side parts 8, and the waist portion D has the waist elastic member 71 disposed therein. This configuration prevents the area between the extensible side parts and its vicinities from bunching up or wrinkling and therefore prevents a gap from being formed between the wearer's body and the inner surface of the diaper even when the diaper is put on with the first section B going in the front of a wearer. As a result, the diaper is highly leakproof especially when put on with the first section B going in the front of a wearer. Where the absorbent member 4 does not occupy a major part of the area between the extensible side parts 8, a gap is apt to be formed in, for example, the part indicated by symbol P in FIG. 4 (i.e., the part between the waist elastic member and the absorbent member).

It is generally believed that extension of an absorbent member to the vicinities of the extensible side parts with approximately the same stiffness as the absorbent member in the crotch section A possesses would impair the extensibility of the elastic members in response to the fastening tapes being pulled, thereby reducing its leakproof properties, an essential function required of a diaper. One skilled in the art would not think of such arrangement of an absorbent member in ordinary disposable diapers. Whereas in the disposable diaper of the present invention that is designed to be fastened on not only the stomach side but the back side of a wearer, it has unexpectedly turned out that the presence of an absorbent member in the vicinity of the extensible side parts results in improved safety against leakage. This is considered to be because the presence of the absorbent member in that area rather prevents the diaper from bunching or wrinkling. It follows that the diaper gives a snug fit, hardly forming a gap with the wearer's body. Where the diaper is fastened on the stomach side, that is, where the extensible side parts go in the back, it is considered that the change of the back waist size depending on the wearer's position is small and thus the a gap hardly generates. Because the front waist size of a wearer largely changes depending on the wearer's position, and the body has a curved surface on the stomach side, a gap is apt to be formed unless an absorbent member is disposed there.

In the disposable diaper 1 according to an embodiment of the present invention, the below-waist elastic members 81 are fixedly held between two sheets integrated with the main body 10 having the topsheet 2, the backsheet 3, and the absorbent member 4, thereby to provide the main body 10 with elastic extensibility. Unlike the configurations in which a separately prepared elastically extensible member is joined to each side of the main body of a disposable diaper as disclosed in JP-T-9-507409 and JP-A-6-63077, the extensible side parts are prevented from being broken even when the fastening tapes 5 are pulled strongly in cases, for example, where one has to put a diaper hastily on an infant crawling about.

Materials of the members making up the disposable diaper 1 according to an embodiment of the present invention will then be described.

The materials for forming the topsheet 2, the backsheet 3, the absorbent member 4, the sheet 62 and the elastic members 61 for forming standing gathers, the landing tape for forming the landing zone 53, and the like are not limited and selected appropriately from known materials commonly used in conventional disposable diapers.

Absorbent members having a certain stiffness are used as the absorbent member 4. For example, an absorbent member made of a fiber aggregate or a combination of a fiber aggregate and a superabsorbent polymer is useful. The fiber aggregate includes nonwoven fabrics or fiber webs prepared by various processes. In using a superabsorbent polymer, the polymer may be dispersed in the interstices of a fiber aggregate or sandwiched in the form of a layer between nonwoven fabrics or fiber webs made of fibrous materials. The absorbent member comprising a fiber aggregate or a combination of a fiber aggregate and a superabsorbent polymer is preferably wrapped in a soft sheet of paper or liquid-permeable nonwoven fabric. In this case, the part of the wrapping sheet extending from the edges of the fiber aggregate is not regarded as part of the absorbent member.

In using an absorbent member made solely of a fiber aggregate, it should preferably have a basis weight of at least 80 g/m$^2$.

The fastening tape 5 includes a tape having a male member (hook) of a mechanical fastener and a tape having a self-adhesive layer formed by applying a self-adhesive. It is likely that a fastening tape with a self-adhesive layer sticks to a one's hand, making it difficult to carry out fastening in a front-to-back way. To avoid this, fastening tapes that can be mechanically engaged on the landing zone 53, such as those having a male member of a mechanical fastener, are preferred. Where the outer surface of the backsheet 3 is made of an engageable material such as nonwoven fabric, that surface can serve as a landing zone 53 for the mechanical fasteners.

The elastic members 71, 81, and 9 for forming the waist gathers, the extensible side parts, and the leg gathers, respectively, are known and conventional. Useful forms of these elastic members include threads (e.g., rubber threads), tapes or strips of some width (e.g., rubber strips), and films. Materials of the elastic members include natural rubber, synthetic rubbers (e.g., styrene-butadiene, butadiene, isoprene or neoprene rubbers), ethylene-vinyl acetate copolymers, extensible polyolefins, and urethane rubber.

The waist elastic member 71 is preferably an elastic strip having a predetermined width. A foamed urethane strip is particularly preferred. The below-waist elastic members 81 are preferably elastic threads. The leg elastic members 9 are preferably rubber tapes. The number of the elastic threads 81 per extensible side part 8 is preferably from about 3 to 12.

While the present invention has been described with reference to a specific preferred embodiment thereof, various changes and modifications can be made therein without departing from the spirit and the scope thereof.

For example, the waist elastic member 71 may be elastic threads in place of the urethane foam strip. The leg elastic members 9 may be arranged to depict a curve along each arched side edge of the crotch section A. The sections, portions, and parts and the other members constituting the disposable diaper of the invention are also subject to variation in shape or configuration.

The disposable diaper according to the present invention is, while applicable to a wide range of wearers from newborns to adults, suited for babies and infants, especially those who are prone to hate or dislike being diapered.

The present invention will now be illustrated in greater detail with reference to Examples. The following Examples are presented as being exemplary of the present invention and should not be considered as limiting.

EXAMPLE 1

Disposable diapers shown in FIGS. 1 and 2 were prepared using the same materials as those of a commercially available fitted disposable diaper (Merries Morenai-Fit®, size M, available from Kao Corp.). The dimensions and configuration of the members making up the diapers were as follows.

L3 (width of each extensible side part 8 measured in the diaper length direction): 3 cm L4 (width of the part of the absorbent member located between extensible side parts 8, measured in the diaper length direction): 2.1 cm L5 (distance between the end 42*a* of the absorbent member and the nearer longer side edge of waist elastic member 71): 2.4 cm Length of each extensible side part 8 measured across the diaper: 9 cm W1 (width of the absorbent member in the part located between extensible side parts 8, measured across the diaper): 12.5 cm W2 (minimum width of the absorbent member in the part located in the crotch section A): 10 cm Distance between the longitudinal end 11 of the diaper and the longitudinal end 42a of absorbent member in the first section B: 40 mm Distance between the longitudinal end 12 of the diaper and the longitudinal end 42b of absorbent member in the second section C: 40 mm One of the disposable diapers was cut at the crosswise centerline CL into equal halves (section F containing the first section B and section G containing the second section C), and the saturated absorption capacity of each half was determined. The F/G saturated absorption capacity ratio was found to be 49/51.

The natural length and the stretched length (both as defined above) of the waist elastic member 71 (made of urethane foam) were 191 mm and 305 mm, respectively, giving the natural length to stretched length ratio of 63%. The tensile load of the below-waist portion E was greater than that of the waist portion D.

COMPARATIVE EXAMPLE 1

Disposable diapers were prepared in the same manner as in Example 1, except that the dimensions and configuration of the constituent members were as follows.

L3 (width of each extensible side part 8 measured in the diaper length direction): 3 cm L4 (width of the part of the absorbent member located between extensible side parts 8, measured in the diaper length direction): 0.8 cm L5 (distance between the end 42a of the absorbent member and the nearer longer side edge of waist elastic member 71): 3.8 cm Length of each extensible side part 8 measured across the diaper: 9 cm W1 (width of the part of the absorbent member located between extensible side parts 8, measured across the diaper): 12.5 cm W2 (minimum width of the absorbent member located in the crotch section A): 10 cm Distance between the longitudinal end 11 of the diaper and the longitudinal end 42a of absorbent member in the first section B: 60 mm Distance between the longitudinal end 12 of the diaper and the longitudinal end 42b of absorbent member in the second section C: 40 mm The F/G saturated absorption capacity ratio of the diaper was 46/54.

COMPARATIVE EXAMPLE 2

Disposable diapers were prepared in the same manner as in Example 1, except that the natural length and the stretched length of the waist elastic member were 139 mm and 305 mm, respectively, giving the natural length to stretched length ratio of 46%.

The diapers prepared in Example 1 and Comparative Examples 1 and 2 were evaluated for (1) leakproofness, (2) ease to put on from the back of a wearer, and (3) resistance against sliding down on a body in motion according to the test methods described below. The results obtained are shown in Table 1.

(1) Ability to Prevent Leakage

A simulated infant hip model was used for testing. The model is shaped to the hips and buttocks of an infant and is designed to discharge artificial urine through a tube from the crotch. The disposable diaper was put on the model in a back-to-front way (the first section B going in the back, and the fastening tapes fastened onto the landing zone on the stomach side) and a front-to-back way (the first section B going in the front).

The model with the diaper on was laid on its stomach, and 40 g of artificial urine was poured at a rate of 5 g/sec. On completion of the pouring, the model was inspected with the naked eye to see if any leak occurred. Where no leak was observed, an additional 40 g of artificial urine was poured after 5 minutes from the end of the first pouring. The pouring operation was repeated, and the total amount of the artificial urine poured until a leak occurred was taken as a measure of the ability against leakage from the front (hereinafter referred to as front leakproofness).

(2) Ease to Put on from the Back

The diaper was placed on a floor, and the same model as used above was put thereon with its stomach down. The fastening tapes were fastened to the landing zone on the back side of the model. The ease of diapering in this way was rated "high" or "low".

(3) Sliding Down on Body in Motion

A simulated infant hip model was used for testing. The model is shaped to the hips and buttocks of an infant and is designed to perform a walking movement in a standing position and to discharge artificial urine through a tube from the crotch. The diaper was put on the model in a front-to-back way. The front top end of the diaper was positioned on the level of the navel. The model was operated to make a 5-minute walking movement at a pace of 150 steps per minute. After stopping the walking movement, 80 g of artificial urine was poured through the tube at a rate of 5 g/sec, and the model was again operated to make the same walking movement for 5 minutes. Thereafter, the sliding distance between the navel and the front top end of the diaper was measured.

TABLE 1

|  | Example 1 | Comparative Example 1 | Comparative Example 2 |
|---|---|---|---|
| Saturated Absorption Capacity Ratio (F/G) | 49/51 | 46/54 | 49/51 |
| Natural Length/Stretched Length of Waist Elastic Member (%) | 63 | 63 | 46 |
| Front Leakproofness in Back-to-front Diapering (g) | 200 | 200 | 200 |
| Front Leakproofness in Front-to-back Diapering (g) | 200 | 160 | 200 |
| Ease of Front-to-back Diapering | high | low | low |
| Sliding Distance in Front-to-back Diapering (mm) | 10 | 20 | 10 |

In the diaper of Example 1, the absorbent member between the extensible side parts prevents the below-waist portion from being gathered too much, assuring ease of picking up and pulling the fastening tapes. Besides, the waist gathers are such that the diaper gives a snug fit in conformity to the wearer's body. As a result, the diaper of Example 1 was able to be put on extremely smoothly and was thus rated "high" in ease of front-to-back diapering. The diaper of Comparative Example 1, on the other hand, was rated "low" in ease of front-to-back diapering because the extensible side parts were gathered too much so that one found it was not easy and took time to pick up the fastening tapes and complete diapering. The diaper of Comparative Example 2 was also rated "low" because the waist portion was gathered so as to make it difficult to apply the diaper to the stomach and the back.

It is seen from Table 1 that the diaper of the present invention is easy to put on from the back of a wearer and hardly leaks whether it is put on from the front or the back of a wearer. On the other hand, the diapers of Comparative Examples 1 and 2 is not easy to put on from the back, and the diaper of Comparative Example 1 is leaky when put on from the back.

EXAMPLE 2

Disposable diapers were prepared in the same manner as in Example 1, except that the absorbent member located between the extensible side parts had a flexural stiffness of 40 gf/50 mm as measured on a specimen cut out of the area from the longitudinal end 42a to 50 mm inward in the first section B.

The absorbent member of Example 1 had a flexural stiffness of 20 gf/50 mm as measured on a specimen cut out of the same area as described above. In both the diapers of Examples 1 and 2, the tensile load of the below-waist portion was 300 gf.

The disposable diaper of Example 2 was evaluated for its ease of front-to-back diapering and resistance to sliding down on a wearer's body in motion when put on front-to-back in the same manner as in Example 1. Table 2 below shows the results obtained together with the results of Example 1.

TABLE 2

|  | Example 1 | Example 2 |
| --- | --- | --- |
| Absorbent Member Bending Stiffness (gf/50 mm) | 20 | 40 |
| Ease of Front-to-back Diapering | high | high |
| Sliding Distance in Front-to-back Diapering (mm) | 10 | 25 |

The disposable diaper according to embodiments of the present invention is easy to put on a wearer whether the portion having fastening tapes goes in the front or the back of the wearer and hardly leaks whichever way of diapering is followed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application Nos. 2002-218959 filed Jul. 26, 2002, 2003-27631 filed Feb. 4, 2003 and 2003-139690 filed May 16, 2003, which are incorporated herein by reference.

What is claimed is:

1. A disposable diaper capable of being put on from either the front or the back of a wearer comprising a liquid permeable topsheet, a liquid impermeable backsheet, a liquid retentive absorbent member interposed between the topsheet and the backsheet, said diaper having a pair of longitudinal side portions and a pair of longitudinal end sections with each respective side portion and said each longitudinal end section having a side edge, and a crotch section located between said longitudinal end sections, and a fastening tape provided on each side edge of one of the longitudinal end section thereof, a gather-forming sheet fixed to said topsheet in a manner parallel to the longitudinal direction of said diaper, said longitudinal end section of said diaper having the fastening tapes having a waist elastic member provided in a waist portion thereof to form an extensible waist part, said waist elastic member being provided in its stretched state over the width of the diaper, and being fixedly sandwiched between said backsheet and said topsheet or said gather-forming sheet, and said longitudinal end section having the fastening tapes also having an extensible side part containing a plurality of elastic members formed in each of a pair of side areas at a below-waist portion thereof, each said extensible side part being fixed in a stretched state and fixedly sandwiched between two sheets of said main body comprised of said topsheet, said backsheet and said absorbent member, and said waist and below-waist elastic members being arranged in parallel with said diaper width direction, wherein each said fastening tape has a basal part fixed between two sheets in a main body of the diaper, and wherein each of a plurality of elastic members that are contained in said extensible side part is disposed in the area between opposing basal parts of each said fastening tape, the absorbent member is disposed such that its longitudinal end in the longitudinal end section having the fastening tapes is nearer to the waist portion of that section than a centerline parallel to a diaper width direction and dividing each of the extensible side parts into equal halves, a width of the absorbent member located between the pair of extensible side parts is equal to or greater than a minimum width of the absorbent member located in the crotch section of the diaper, and a portion of said absorbent member intermediate said ends thereof being narrowed along the width direction, two portions on opposite sides of a centerline dividing the length of the diaper in equal halves have a saturated absorption capacity ratio of from 45/55 to 55/45, the absorbent member has a flexural stiffness of from 3 to 25 gf/50 mm as measured on a specimen cut out of the area from the longitudinal end of the absorbent member in the section having the fastening tapes to 50 mm inward in accordance with JIS K7171, and a natural length of the waist elastic member in a state removed from the diaper is from 60 to 80% of a length of the waist elastic member as provided as part of the diaper, the tensile load required to extend the below-waist portion in the longitudinal section having the fastening tapes to an extension ratio of 30% lower than the maximum extension ratio is higher than that required to extend the waist portion in the same section to an extension ratio 30% lower than the maximum extension ratio, and in the longitudinal section having the fastening tapes, the length of the waist elastic member in the widthwise direction is longer than the length of the absorbent member in the widthwise direction.

2. The disposable diaper according to claim 1, wherein the distance from a longitudinal end of the absorbent member to a longitudinal end of the diaper in one of the longitudinal end sections thereof, and that in the other longitudinal end section is substantially equal.

3. The disposable diaper according to claim 1, wherein the waist elastic member is an elastic strip comprising urethane foam.

4. The disposable diaper according to claim 1, wherein the waist elastic member is disposed in the area between the two basal parts.

* * * * *